United States Patent
Bouquet et al.

(10) Patent No.: US 6,280,970 B1
(45) Date of Patent: Aug. 28, 2001

(54) IMMORTALIZED AVIAN CELL LINES

(75) Inventors: Jean-François Bouquet, $S_{te}$-Consorce; Miloud Benchaïbi, Strasbourg; Jacques Samarut, Villeurbanne; Philippe Desmettre, Ecully, all of (FR)

(73) Assignee: Institut Naltional de la Recherche Agronomiqe, Paris (FR)

( * ) Notice: Subject to any disclaimer, the term of this patent is extended or adjusted under 35 U.S.C. 154(b) by 0 days.

(21) Appl. No.: 09/194,020
(22) PCT Filed: May 22, 1997
(86) PCT No.: PCT/FR97/00898
§ 371 Date: Jun. 23, 1999
§ 102(e) Date: Jun. 23, 1999
(87) PCT Pub. No.: WO97/44444
PCT Pub. Date: Nov. 27, 1997

(30) Foreign Application Priority Data

May 23, 1996 (FR) .................................................. 96 06629

(51) Int. Cl.[7] ................ C12N 5/16; C12P 21/00
(52) U.S. Cl. .................... 435/69.1; 435/349; 435/235.1; 435/320.1; 435/455
(58) Field of Search ................ 435/349, 320.1, 435/69.1, 235.1, 325, 455

(56) References Cited

FOREIGN PATENT DOCUMENTS 0 242 272 A1  10/1987  (EP) .
WO 91/18971  12/1991  (WO) .
WO 92/10563   6/1992  (WO) .
WO 93/20200  10/1993  (WO) .

OTHER PUBLICATIONS

"The 12S adenoviral E1A protein immortalizes avian cells and interacts with the avian RB product", Guilhot et al, *Oncogene*, 1993, vol. 8, pp. 619–624.

"Human membrane cofactor protein (CD46) acts as a cellular receptor for measles virus", Naniche et al, *Journal of Virology*, Oct. 1993, pp. 6025–6032.

"Immortalization of human fibroblasts transformed by origin–defective simian virus 40", Neufeld et al, *Molecular and Cellular Biology*, Aug. 1987, pp. 2794–2802.

"Overexpression of human cyclin A advances entry into S phase", Rosenberg et al, *Oncogene* , vol. 10, pp. 1501–1509.

"Activation of Epstein–Barr virus latent genes protects human B cells from death by apoptosis", Gregory et al, *Nature*, Feb. 2, 1991, vol. 349, pp. 612–614.

*Primary Examiner*—Donna C. Wortman
*Assistant Examiner*—Robert A. Zeman
(74) *Attorney, Agent, or Firm*—Larson & Taylor PLC

(57) ABSTRACT

The invention features non-transformant immortal avian cells, in particular derived from avian tissues, i.e. other than blood or haemotopoietic cells, particularly fibroblasts and epithelial cells, for instance of embryos. The avian cells are immortalized by the SV40 T+t gene in the dependence of the MTI promoter. In particular they integrate the pDAMT vector.

14 Claims, 1 Drawing Sheet

IMMORTALIZED AVIAN CELL LINES

Figure 1:
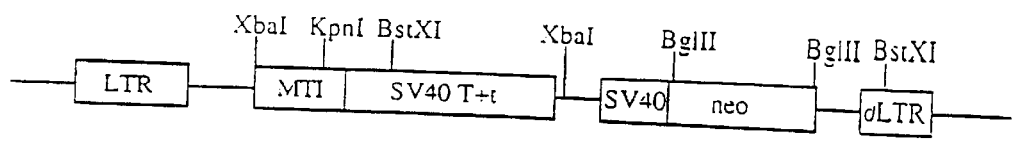

The present invention relates to an avian cell line and its derivatives.

It is not possible to establish cell lines spontaneously from organs taken from avian species, as can be done in the case of some organs derived from mammalian species.

The only available cell lines to date were obtained using the transforming properties of certain avian viruses which possess oncogenic properties, such as the retroviruses of the avian leukosis group or Marek's disease virus, or certain chemical molecules such as methylcholanthrene and diethylnitrosamine.

For the most part, these cell lines are considerably transformed, which renders them unsuitable for multiplying vaccine viruses.

Authors are adopting a novel approach which consists in introducing into cells a vector which does not exhibit any oncogenic character but which is able to integrate, into these cells, a gene which is selected for its capacity to induce immortalization.

The first tests were carried out using vectors which integrate avian retrovirus genes such as erbA and erbB.

French Patent Application FR-A-2 596 770 proposes an immortalization method in which a culture of avian or mammalian cells is infected with a vector or a system which, while not being oncogenic for the said cells, is able to integrate a gene selected from v-myb, v-ets and v-erbA into these cells. The AMV, E26 and XJ12 viruses, with this latter being a virus derivative of the AEV virus in which the oncogenic v-erB gene has been deleted, can be appropriate vectors.

In practice, while these tests made it possible to obtain established cell lines from cells of the haematopoietic cell line, they did not give the expected results in the case of chick embryo cells in adherent culture, such as fibroblasts or epithelial cells.

It was possible to obtain untransformed avian cell lines of the myeloblastoid type (blood cells) using the oncogene myb (International Patent Application WO91/18971).

In parallel, authors have proposed using the early t and T genes of the simian virus SV40 for immortalizing cells derived from different mammalian tissues (D. S. Neufeld et al., Molecular and Cellular Biology, August 1987, 2794–2802, O. Kellermann and F. Kelly, Differentiation 1986, 32: 74–81 and French Patent Application FR-A-2 649 721).

For its part, French Patent Application FR-A-2 649 721 proposes a method of conditional immortalization which, it is claimed, can be used for any cell type and in any species, with the aim in this case being that of remedying the drawback of the high degree of specificity of the conventional approaches (limitation to particular species and/or to particular cell types): transformation of cells with a transforming virus (adenovirus, Epstein-Barr virus, certain papovaviruses such as the SV40 virus or polyoma virus; for example, the SV40 virus is indicated as only transforming rodent cells and human cells); transfection with constructs which contain a transforming gene which is linked to a viral promoter; transfection with a transforming gene which is linked to a cellular promoter. The choice of this patent application falls on a construct which combines a DNA fragment from the regulatory sequence of vimentin and a DNA fragment which encodes an immortalizing gene, which construct can be the T antigen of the SV40 virus under the control of the inducible promoter of vimentin. This document never mentions the avian species.

The actual use of such viral oncogenes has never been described in the avian species, apart from the use of the 12 S form of the E1A protein of human adenovirus 5, which made it possible to immortalize quail epithelial cells (Guilhot et al. (1993), Oncogene 8: 619–624).

Contrary to all expectations, the inventors succeeded in producing an immortal, untransformed avian cell line.

More generally, the inventors have found that it was possible to prepare immortal, untransformed avian cell lines even from cells of avian tissues, that is to say from cells other than circulating blood cells or haematopoietic cells.

The present invention therefore relates to the immortal, untransformed avian cells which derive, in particular, from avian tissues, that is to say from cells other than blood cells or haematopoietic cells, in particular fibroblasts and epithelial cells, for example from embryos.

The present invention relates, in particular, to immortal, untransformed avian cells which contain, integrated into their genome, the SV40 T+t gene under the control of the MTI (murine metallothionein I) promoter.

Preferably, the cells also integrate the SV40 promoter, which is functionally linked to the gene for resistance to neomycin.

Preferably, the cells also integrate at least one LTR sequence. The LTR sequence can be deleted as described in the examples.

The cells preferably integrate the vector pDAMT which is depicted in FIG. 1.

While the cells are of avian origin, they may in particular be derived from Muscovy duck.

The invention relates, more especially, to the immortal, untransformed avian cell line TDF-2A, which is deposited in the CNCM (Collection Nationale de Cultures de Microorganismes de l'Institut Pasteur (Pasteur Institute National Collection of Microorganism Cultures)) under reference number I-1712.

The invention naturally covers the cells which are derived from these cell lines. By this, it is to be understood that it is not only the cells as deposited in the CNCM under the indicated references which are covered but also the cells which constitute the progeny of these deposited cells, i.e., on the one hand, those which are obtained by simple multiplication and which may undergo mutations during these multiplications and, on the other hand, those which are obtained after deliberate modification, which are then termed derived cells, and, of course, also those which have undergone the two types of modification.

The invention therefore also covers the derived cells which are obtained by modifications of the above cells. These modifications may consist in:

Inserting one or more expression cassettes, each of which comprises one or more nucleotide sequences encoding a molecule of industrial relevance, with these expression cassettes being able to produce this molecule following insertion into the cells of the invention. The skilled person is fully conversant with the technique. Molecules of industrial relevance which may be mentioned, in particular, are viral subunits of the peptide, protein or glycoprotein type, in particular for use in a vaccine or a diagnostic reagent, protein molecules such as hormones, etc.

Chronically infecting with a virus which is able to multiply in the cells, for virus or vaccine production purposes, with or without prior modification of the sensitivity towards this virus. The infection may also not be chronic but carried out on a batch of cells which is selected for the viral multiplication. (The modifications described below are to be understood as preferably and advantageously being combined with the preceding two types of modification).

Introducing survival or anti-apoptotic genes other than bcl-2, such as the genes which encode the human adenovirus p19E1B (Rao et al. (1992), Proc. Natl. Acad. Sci. USA 89: 7742–7746), the Epstein Barr virus LMP-1 (Gregory et al. (1991), Nature 349: 612–614) and BHRF1 (Pearson et al. (1987), Virology 160: 151–161), the herpes simplex virus ICP34.5 (Chou and Roizman (1992), Proc. Natl. Acad. Sci. USA 89: 3266–3270) and the baculovirus p35 (Clem et al. (1991), Science 254: 1388–1390) proteins in order to render these cell lines more resistant to the culture conditions, in particular for maintaining confluence.

Overexpressing genes which are involved in controlling the cell cycle using vectors which are suitable for increasing the rate of proliferation. Thus, it has been demonstrated that, in certain cases, overexpressing cyclin-encoding genes leads to the cell cycle being shortened and therefore to the rate of proliferation being increased (Rosenberg et al. (1995), Oncogene 10: 1501–1509; Quelle et al. (1993), Genes and Dev. 7: 1559–1571).

Modifying the viral sensitivity spectrum of the cell lines by integrating genes which encode receptors for the viruses of interest, with a view to multiplying these viruses.

Reference may be made to the mammalian species, where expression of the receptor for the measles virus (CD46) by murine cells, which are normally non-permissive for the virus, results in these cells becoming sensitive to this virus and being able to replicate it (Naniche et al. (1993), J. Virol. 67: 6025–6032). The interest is, in particular, in rendering cells sensitive to a virus in order to produce the virus on these cells.

Integrating oncogenes which are able to accelerate cell growth.

It is self-evident that the derived cells according to the invention may comprise one or more of the above-described modifications.

The invention also relates to a method for producing molecules of industrial relevance or viruses, which method comprises culturing the above-described cells.

The present invention is directed, in particular, towards producing molecules or viruses for creating diagnostic reagents or vaccines, or else towards producing molecules of therapeutic relevance.

The invention will now be described in more detail with the aid of an embodiment which is taken by way of non-limiting example and with reference to FIG. 1, which shows the structure of the vector pDAMT, which is used to prepare the cell line TDF-2A, and in which:

LTR: direct repeat sequence (long terminal repeat)
LTR: deleted LTR
MTI: murine metallothionein I promoter
SV40 T+t: SV40 early region
SV40: SV40 promoter

EXAMPLE 1

Production of the TDF-2 A Cell Line

I. Description of its Origin and its Characteristics
1.1 Description of the Vector Employed: Vector pDAMT It comprises the SV40 virus early region (encodes the T and t antigens) (HindIII/BamHI fragment) (Fiers et al. (1978), Nature 273: 113–120) under the control of the mouse metallothionein I promoter (EcoRI/BglII fragment with the BglII site being transformed into a HindIII site) (Durnam et al. (1980), Proc. Natl. Acad. Sci. USA 77: 6511–6515 ; Brinster et al. (1982), Nature 296: 39–42).

The EcoRI/EcoRI fragment containing this transcription unit, derived from the vector pMTSVneo (Peden et al. (1989), Exp. Cell. Res. 185: 60–72), was inserted into the XbaI site of the vector pDA1 (Aubert et al. (1991), J. Cell. Biol. 113: 497–506). This latter vector is essentially derived from the genome of the Rous sarcoma-associated virus 2 (RAV-2) following modification of the 3' LTR. Thus, the U3 region of the RAV-2 3' LTR was deleted and linked to the R and U5 regions isolated from the Rous sarcoma-associated virus 1 (RAV-1) LTR. The vector also carries a transcription unit which contains the gene for resistance to neomycin under the control of the SV40 promoter derived from the vector pSV2neo (Southern and Berg (1982), J. Mol. Appl. Genet. 1: 327–341). See FIG. 1.

1.2. Establishment of the Cell Line and Demonstration that it is Immortalized.

Cells derived from 14-day Muscovy duck embryos were transfected with vector pDAMT using the dimethyl sulphoxide (DMSO) method described by Kawai and Nishizawa (1984), Mol. Cell. Biol. 4: 1172–1174. The transfected cells are then selected by applying geneticin G418 (150 µg/ml) for 15 days. The resistant clones are then subcultured regularly at the rate of from 1 to 2 passages per week. After this 3-month period of active proliferation, the cells entered into a crisis period during which most of the cells died. After this period, which lasted approximately 2 months, several clones resumed active proliferation, suggesting that they had been immortalized.

The TDF-2 A cell line is thus derived from 2 cultures. It was studied in more depth.

The TDF-2 A cells achieved 200 passages, that is approximately 460 generations, and were thus maintained continuously in culture for more than 600 days. By comparison, control cells, which are not expressing the SV40 virus early region, cannot be maintained in culture for more than 20 passages.

1.3. Proliferation Characteristics.

The immortalized cells are cultured at 38° C., in a roller bottle, in a medium containing 6% 10×HAM F-10, 4% 10×199 HANKS, from 2.95% to 4% tryptose broth phosphate, from 5.6% to 2.5% sodium bicarbonate, 0.1% 100×vitamin BME, 3% foetal calf serum, from 5% to 1% kanamycin and from 0.5% to 1% vancomycin.

Under these conditions, their rate of doubling is once every 24 hours.

1.4. Expression of the T Antigen

It was verified, by means of indirect immunofluorescence or indirect immunophosphatase using an antibody which is specific for the T antigen (Pab 101: Santa Cruz Biotechnology ref. sc147), that all the cells express the T antigen in their nucleus, indicating that they have all integrated the vector.

This integration was additionally demonstrated by means of Southern blotting. The genomic DNA of the immortalized fibroblasts was digested with the restriction enzymes XbaI and BstXI. Hybridization with a probe which was specific for the T antigen (1018 bp NdeI/NdeI fragment) verified that the transcription unit, which expressed the immortalizing gene and which was inserted into the TDF-2A cells, had not undergone any major rear-rangements. This was indicated by the fact that the sizes of the hybridization fragments obtained were in accordance with the expected sizes.

1.5. Absence of Tumorigenic Capacity.

The immortalized cells do not exhibit any tumorigenic capacity. They are incapable of forming colonies in semi-solid medium or of forming tumours on hen or duck egg chorioallantoic membrane. They are also incapable of forming tumours on nude mice, and one-day old SPF (pathogen-free) ducklings and chicks.

1.6. Karyotype.

The karyotype of the TDF-2A cells was studied at the 114th and 135th passages. This verified that the cells were indeed of avian origin, with the microchromosomes characteristic of this species being present. Furthermore, the chromosomes which were observed are representative of the chromosomes which are encountered in primary duck embryo cells, thereby confirming the origin of the cell line.

II. Properties

The TDF-2A cells exhibit, in particular, a sensitivity to the duck-specific viruses, such as adenovirus, parvovirus and reovirus, which are customarily replicated on primary duck embryo cells. These viruses can therefore be produced on this cell line.

EXAMPLE 2

Characterization of the TDF-2A Cell Line by Identifying the Integration Sites

The genomic DNA of the TDF-2A cells, which was prepared from cells derived from the 114th and 135th passages, was digested with the restriction enzymes BglII and KpnI. The DNA, which had been treated in this way, was then subjected to gel electrophoresis, followed by transfer to a nylon membrane; it was then hybridized with a probe which was specific for the T antigen (1018 bp NdeI/NdeI fragment). For example, digestion with BgIII gives rise to two hybridization bands of large size (approximately 15 and 23 kb), suggesting the existence of two integration sites. Digestion with KpnI gives rise to one major band of large size (approximately 20 kb) and to at least one minor band, thereby confirming the existence of at least two integration sites.

EXAMPLE 3

Multiplication of Adenovirus V127 on TDF-2A Cells

The TDF-2A cells are seeded in a roller bottle.

Soft-shelled egg disease adenovirus strain V127 is inoculated into the cell culture. After 6 days, harvestis ing is carried out by shaking in order to detach the cell lawn. The harvested mixture therefore consists of the cell lawn and the culture supernatant. The whole is homogenized by treating with a cell grinder or homogenizer such as Ultraturrax for 1 min at 13,500 rpm (T25-type IKA appliance).

The infectious viral titre is determined by means of a micromethod carried out on 96-well plates. The virus dilutions are inoculated onto a lawn prepared from secondary SPF Muscovy duck embryo cells. Each viral dilution is inoculated into 6 wells. The plates are incubated in a $CO_2$ incubator for 8 days. The presence of the virus in the wells is checked by observing the characteristic cytopathic effect (CPE) under the microscope. The infectious titre is calculated by the KARBER method and is expressed by the logarithm of the inverse of the viral dilution which gives 50% CPE [titre=d+r/Nx(n+N/2)], where d is the dilution expressed in logs when all the wells are positive, r is the dilution ratio, N is the number of wells per dilution and n is the number of positive wells between 0 and 100%.

The presence of the virus is also confirmed by investigating the haemagglutinating activity of the viral supernatant using a suspension of chick red blood corpuscles. In this case, 50 µl of supernatant from the abovementioned wells are deposited on a Dynatech microtitration plate and 25 µl of a suspension of chick erythrocytes containing $15.10^6$ cells/ml are added per well. After the microtitration plate has been shaken and incubated at ambient temperature for 45 min, all the wells which exhibit clearly visible haemagglutination are regarded as being positive. The titre is likewise calculated by the KARBER method. Results: The viral titres which are obtained are equivalent to those obtained on primary duck embryo cells.

What is claimed is:

1. Immortal, but untransformed, avian embryonic fibroblast cells and their progeny, wherein these cells comprise in their genome, the SV 40 T+t gene.

2. Cells according to claim 1, which contain in the cell's genome, the SV40 T+t gene under the control of the MTI promoter.

3. Cells according to claim 1, wherein they also comprise in the cell's genome the SV40 promoter, which is functionally linked to the gene for resistance to neomycin.

4. Cells according to claim 1, wherein they also comprise in the cell's genome at least one LTR sequence.

5. Cells according to claim 1, wherein they contain and express at least one nucleotide sequence.

6. Cells according to claim 5, wherein the nucleotide sequence encodes a viral peptide, protein or glycoprotein.

7. Cells according to claim 1, wherein they are infected with a virus which multiplies in these cells.

8. Cells according to claim 1, which comprise a vector which overexpresses a gene of the cells, which gene is involved in the control of the cell cycle.

9. Cells according to claim 1, wherein they comprise an oncogene.

10. Method for producing a molecule, or a viral peptide, protein or glycoprotein, or a virus, comprising taking a cell according to claim 1, inserting a nucleotide sequence into said cell, culturing said cell and expressing said nucleotide seguence so as to produce a molecule, or a viral peptide, protein or glycoprotein, or a virus.

11. Immortal, untransformed avian cell line TDF-2A, which is deposited in the CNCM (Collection Nationale de Cultures de Microorganismes de l'Institut pasteur (Pasteur Institute national Collection of Microorganism Cultures)) under reference number 1-1712.

12. Immortal, but untransformed, avian embryonic fibroblast cells and their progeny, wherein the cells comprise in their genome a vector consisting essentially of an immortalization gene, a promoter of this gene and LTR sequences.

13. Cells according to claim 12, wherein the immortalization gene is SV40 T+t.

14. Cells according to claim 13, wherein the promoter is the MTI promoter.

* * * * *

UNITED STATES PATENT AND TRADEMARK OFFICE
CERTIFICATE OF CORRECTION

PATENT NO.   : 6,280,970 B1                                                                              Page 1 of 1
DATED        : August 28, 2001
INVENTOR(S)  : Bouquet et al.

It is certified that error appears in the above-identified patent and that said Letters Patent is hereby corrected as shown below:

<u>Title page,</u>
Item [73], Assignee: Institut National De La Recherche Agronomique, Paris, FRANCE
Centre National De La Recherche Scientifique (C.N.R.S.), Paris, FRANCE
Ecole Normale Superieure De Lyon, Lyon, FRANCE
Merial, Lyon, FRANCE Signed and Sealed this Thirtieth Day of July, 2002

*Attest:*

*Attesting Officer*

JAMES E. ROGAN
*Director of the United States Patent and Trademark Office*